United States Patent [19]
Graumann

[11] Patent Number: 5,598,466
[45] Date of Patent: Jan. 28, 1997

[54] VOICE ACTIVITY DETECTOR FOR HALF-DUPLEX AUDIO COMMUNICATION SYSTEM

[75] Inventor: David L. Graumann, Vancouver, Wash.

[73] Assignee: Intel Corporation, Santa Clara, Calif.

[21] Appl. No.: 520,305

[22] Filed: Aug. 28, 1995

[51] Int. Cl.$^6$ .............. H04M 9/10; H04M 9/08; G10L 3/00; G10L 9/18
[52] U.S. Cl. .............. 379/389; 379/351; 381/56; 395/2.42
[58] Field of Search .............. 379/388, 389, 379/390, 406, 414, 416, 351; 395/2.42, 2.35, 2.36, 2.37, 2.17, 2.23; 381/46, 47, 56, 57, 94, 110

[56] References Cited

U.S. PATENT DOCUMENTS

| | | | |
|---|---|---|---|
| 4,028,496 | 6/1977 | LaMarche et al. | 379/406 X |
| 4,147,892 | 4/1979 | Miller | 379/389 |
| 4,461,024 | 7/1984 | Rengger et al. | 395/2.42 |
| 4,630,304 | 12/1986 | Borth et al. | 381/94 |
| 4,672,669 | 6/1987 | DesBlache et al. | 381/46 |
| 4,715,063 | 12/1987 | Haddad et al. | 379/388 X |
| 4,796,287 | 1/1989 | Reesor et al. | 379/390 |
| 4,887,288 | 12/1989 | Erving | 379/389 X |
| 4,959,857 | 9/1990 | Erving et al. | 379/390 |
| 4,979,214 | 12/1990 | Hamilton | 395/2.42 |
| 5,239,574 | 8/1993 | Brandman et al. | 379/351 X |
| 5,255,340 | 10/1993 | Arnaud et al. | 379/351 X |
| 5,293,588 | 3/1994 | Satoh et al. | 395/2.42 |
| 5,297,198 | 3/1994 | Butani et al. | 379/390 X |
| 5,323,337 | 6/1994 | Wilson et al. | 395/2.42 X |
| 5,357,567 | 10/1994 | Barron et al. | 379/390 |
| 5,459,814 | 10/1995 | Gupta et al. | 395/2.42 |
| 5,471,528 | 11/1995 | Reesor | 379/388 X |

OTHER PUBLICATIONS

Rabiner et al., "Digital Processing of Speech Signals", 1st ed., 1978, pp. 130–135 1978.
R. J. Johnson et al., "Speech Detector", IBM Technical Disclosure Bulletin, vol. 22, No. 7, Dec. 1979, pp. 2624–2625 Dec. 1979.

Primary Examiner—Krista M. Zele
Assistant Examiner—Devendra Kumar
Attorney, Agent, or Firm—Blakely, Sokoloff, Taylor & Zafman

[57] ABSTRACT

A method of detecting voice in an audio signal comprises the steps of determining an average peak value representing an envelope of the audio signal, determining a running instance of audio signal standard deviation, which corresponds to one of a number of overlapping time intervals, and updating a power density function (PDF) by adding instances of noise to the PDF if the average peak of the audio signal exceeds the current level of the audio signal by a certain amount and if the current standard deviation value falls below a threshold for a predetermined time interval. A noise floor is located based on the mean value of the PDF, and, if the audio signal sustains a power level exceeding the noise floor, voice activity is determined to be present in the audio signal. The PDF is updated by a low confidence factor if all of the standard deviation values calculated during a certain period of time are below the threshold value and by a high confidence factor if all standard deviation values within a certain longer period of time period are below the threshold value.

31 Claims, 17 Drawing Sheets

VOICE ACTIVITY DETECTOR FOR HALF-DUPLEX AUDIO COMMUNICATION SYSTEM

FIELD OF THE INVENTION

The present invention pertains to the field of telecommunications. More particularly, the present invention relates to establishing a noise floor and detecting speech activity in an audio signal.

BACKGROUND OF THE INVENTION

Advances in telecommunications technology are continuously improving the ways in which people carry out both business and personal communications. Such advances include improvements in video conferencing, increased availability of ISDN links and computer networks, and improvements in ordinary telephone service. These technological advances create many design challenges. For example, many telecommunication systems require a solution for distinguishing speech from noise in an audio signal; a device which performs this function has been referred to as a voice activity detector (VAD).

One application for a VAD is in a half-duplex audio communication system used in "open audio", or speakerphone, teleconferencing. Half-duplex transmission is transmission which takes place in only one direction at a given point in time. Therefore, it is a common practice in such a system to temporarily deactivate the microphone at a given site while that site is receiving a transmission and to mute the speaker at either site to eliminate audio feedback being received by the remote site. Consequently, a VAD may be necessary to detect the presence of speech both in the audio signal received from a remote site and in the audio signal to be transmitted to the remote site in order to implement these functions. A VAD may also be used to signal an echo suppression algorithm, to distinguish "voiced" speech from "unvoiced" speech, and in various other aspects of audio communications.

Some existing VADs make use of the communication link itself in detecting speech activity. For example, certain data may be provided to a VAD at one end of the link by "piggybacking" the data on other audio data transmitted from the other end. For various reasons, however, it is not desirable to have a VAD which is dependent upon a remote site in detecting speech. In addition, some existing VADs have undesirably slow response times, frequently misclassify speech, or require excessive processing time.

Another design issue relates to the use of headsets to implement closed audio microphone and speakers in video conferencing. Video conferencing software applications are available which, in general, permit both audio and visual communication between the user of one personal computer and the user of another personal computer via ISDN lines, a LAN, or other channels. One such application is the ProShare™ Personal Conferencing Video System, created by Intel Corporation of Santa Clara, California. Some video conferencing applications are sold precalibrated to support one or more particular models of headsets. This precalibration may be accomplished by including data in the software code relating to the appropriate hardware settings, such as the microphone input gain. However, if the user wishes to use a non-supported headset, he or she must generally go outside of the video conferencing application to the operating system in order to adjust the hardware settings. In doing so, the user essentially must guess at the best hardware settings, often having to readjust the settings by trial and error in order to achieve the optimum settings. Hence, existing hardware calibration solutions provide little flexibility in terms of ability to support multiple different headsets.

In view of these and other design issues, therefore, it is desirable to have a VAD which operates independently of the remote site. It is further desirable that such a VAD provide high-accuracy (infrequent misclassifications), fast response time, adaption to the remote site's fluctuating signal-to-noise ratio, and consistent half-duplex performance when the remote user transitions between open and closed audio modes. In addition, it is desirable to provide a VAD which can be directly used by a hardware calibration solution. Finally, it is desirable to have a hardware calibration solution which automatically adjusts the hardware settings to be appropriate for any headset a user wishes to employ.

SUMMARY OF THE INVENTION

An aspect of the present invention is a method of locating a noise floor for qualifying a signal. The method comprises the step of establishing a noise power density function (NPDF), based on (1) a relationship between an approximate peak level of the signal and a current level of the signal, and (2) a number of standard deviation values of the signal. Each of the standard deviation values corresponds to one of a number of time intervals. The method further comprises the steps of repeatedly updating the NPDF to a current state, and using the current state of the NPDF to locate the noise floor.

Another aspect of the present invention is a method of detecting speech in an audio signal. The method comprises the steps of: (1) determining an average peak value of the audio signal; (2) determining a number of standard deviation values of the audio signal, each of which corresponds to one of a number of time intervals; (3) updating a power density function (PDF) to a current state of the PDF, according to: (a) the relationship between the average peak and a current level of the audio signal, and (b) the standard deviation values; (4) locating a noise floor based on the current state of the PDF; and (5) if a certain relationship exists between the current level of the audio signal and the noise floor, determining that speech activity is present in the audio signal.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and apparatus for establishing a noise floor and for detecting speech activity in an audio signal is described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to avoid unnecessarily obscuring the present invention.

Figure 1:
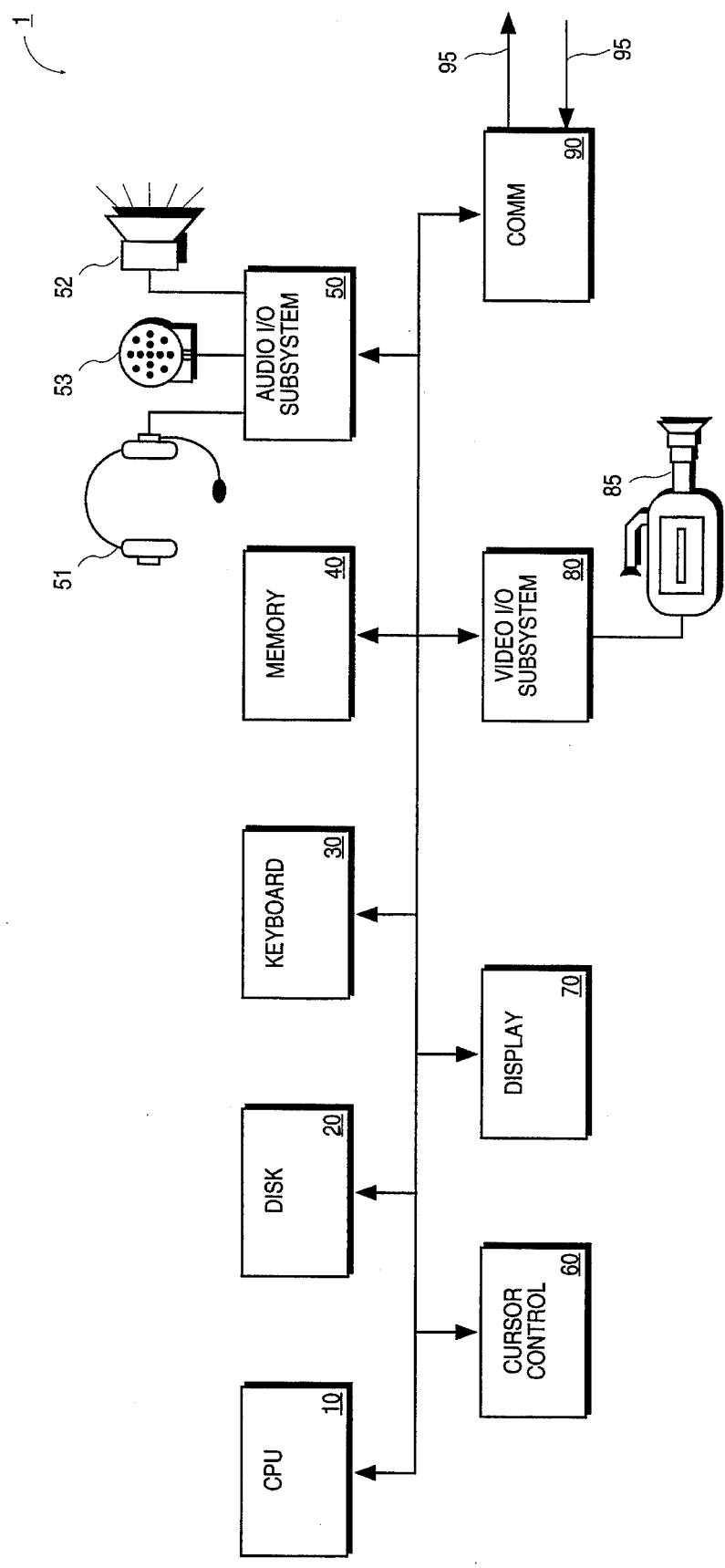
FIG. 1 illustrates a computer system in which the present invention can be implemented.

The present invention is implemented in a computer system 1 having half-duplex audio communication with at least one other computer system through an audio channel 95, as illustrated in FIG. 1. The audio channel 95 may be an Integrated Services Digital Network (ISDN) link or a standard computer local area network (LAN), or an analog phone system. The computer system 1 includes a central processing unit 10, a disk storage device 20, a keyboard 30, a memory 40, an audio input/output (I/O) subsystem 50, a cursor control device 60, a display 70, a video I/O subsystem 80 receiving input from a video camera 85, and an interface device 90, such as a modem, providing an interface between the computer system 1 and the audio channel 95. The audio I/O subsystem 50 is coupled to a speaker 52 and a microphone 53 for open audio communication and to a headset 51 having both a speaker and a microphone for closed audio communication. The cursor control device 60 may be a mouse, trackball, light pen, stylus/graphics tablet, or other similar device. The disk storage device 20 may be a magnetic disk, CD-ROM, or other alternative data storage device.

Figure 2:
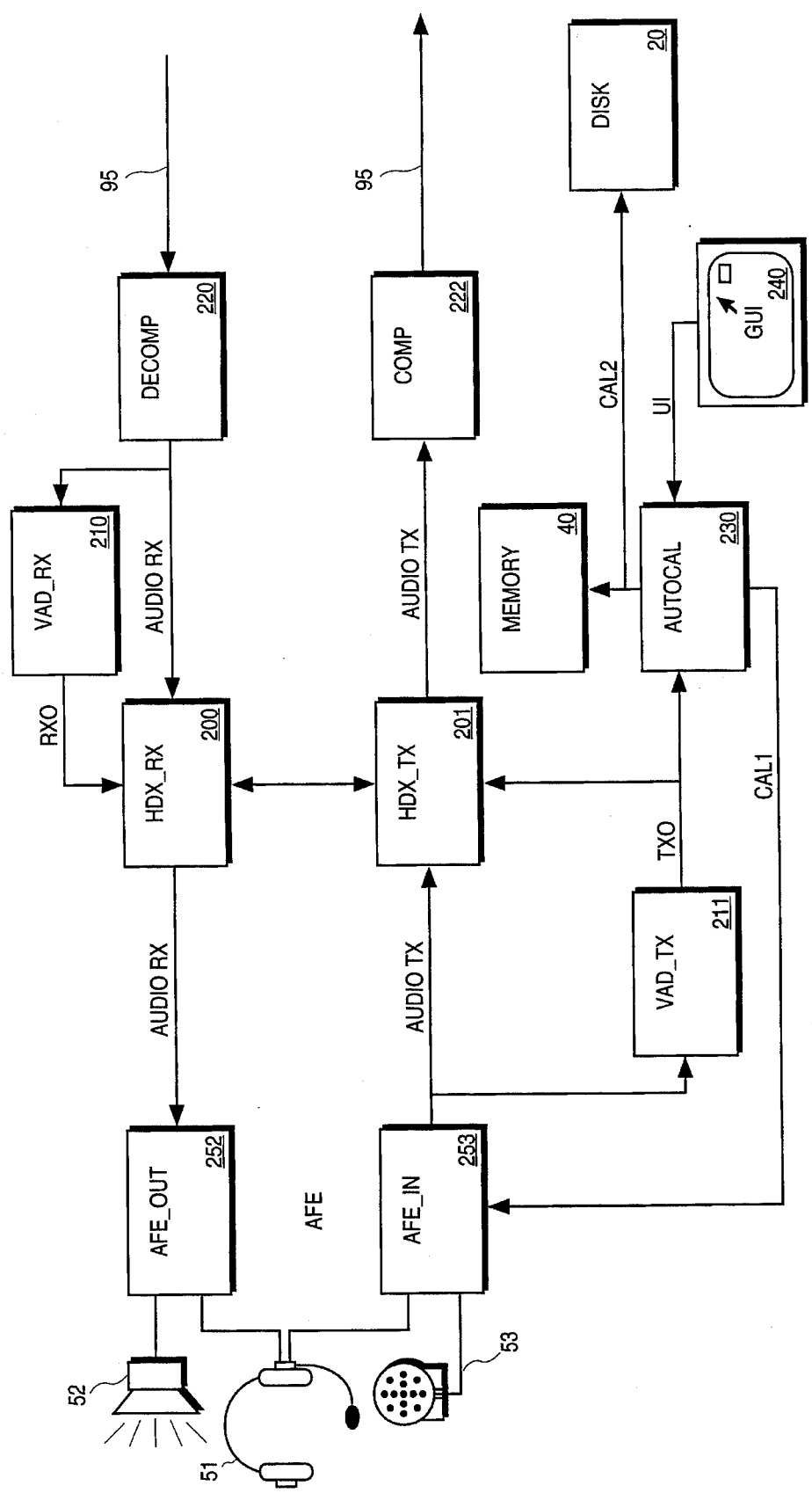
FIG. 2 illustrates the data flow associated with speech detection and automatic calibration of a microphone in a computer system using half-duplex audio communication.
Figure 3:
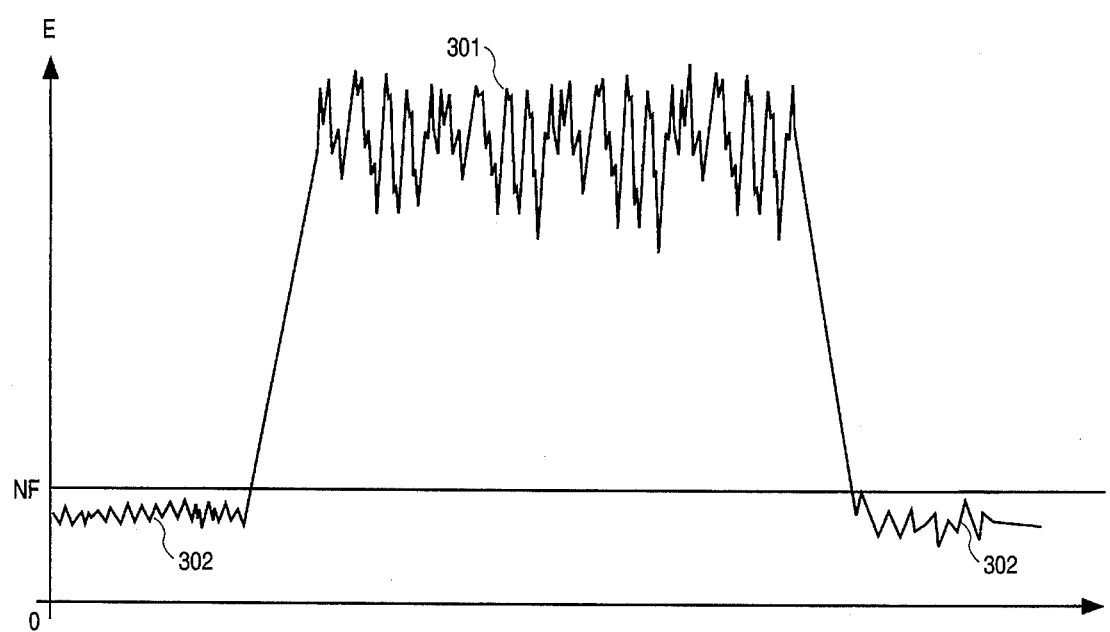
FIG. 3 illustrates a waveform of an audio signal having speech activity.

FIG. 2 illustrates the data flow associated with operation of the present invention. The present invention is implemented in a voice activity detector (VAD) receive channel 210, a VAD transmit channel 211, and an autocalibrator 230, each of which may be embodied in software stored in memory 40 or on the disk storage device 20, or in equivalent circuitry. In FIG. 2, compressed audio data is received by the computer system 1 from the audio channel 95 and input to decompression unit 220. Signal AUDIO RX, which contains decompressed audio data, is then output by decompression unit 220 to half-duplex receive channel 200 and to VAD receive channel 210. The energy E of the signal AUDIO RX has a waveform similar to that illustrated in FIG. 3. In FIG. 3, the portion 301 of the waveform which exceeds a noise floor NF is considered to be speech energy, whereas the portions 302 of the waveform not exceeding the noise floor NF are considered to be only noise energy. The VAD receive channel 210 receives signal AUDIO RX as input and generates an output RXO to half-duplex receive channel 200 indicating whether or not the signal AUDIO RX contains speech at any given point in time.

Figure 4A:
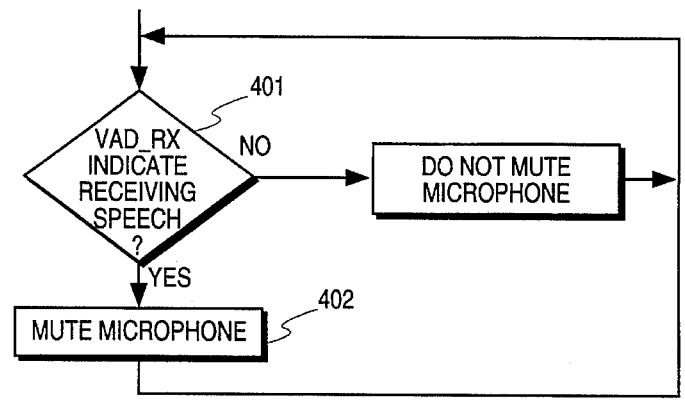
FIGS. 4A and 4B illustrate the function of a voice activity detector (VAD).

The half-duplex receive channel 200 selectively passes on the signal AUDIO RX to audio front-end output circuitry 252 depending upon the output RXO of the VAD receive channel 210. Audio data passed on to audio front-end output circuitry 252 is processed and sent to the speaker 52. Referring now to FIG. 4A, if the VAD receive channel 210 indicates to the half-duplex receive channel 200 that speech is present in the signal AUDIO RX in step 401, then the half-duplex receive channel 200 communicates with half-duplex transmit channel 201 to cause the microphone 53 to be muted in step 402. The microphone 53 remains muted until speech is no longer detected in the signal AUDIO RX.

Figure 4B:
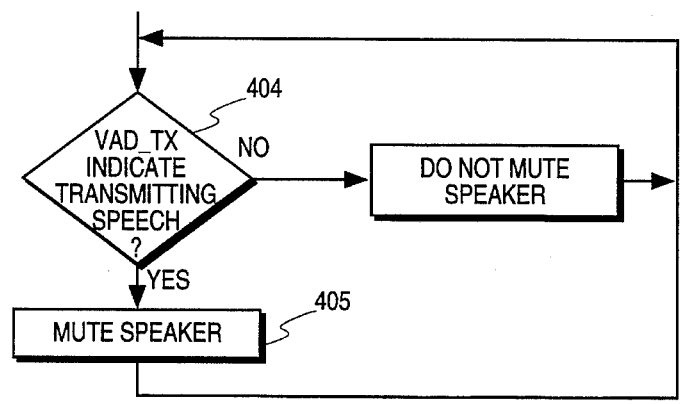

Referring again to FIG. 2, sound to be transmitted across the audio channel 95 is input by a user either through the microphone of the headset 51 or through the open audio microphone 53 into audio front-end input circuitry 253, which outputs the signal AUDIO TX. The energy E of signal AUDIO TX, as with signal AUDIO RX, has a form similar to that depicted in FIG. 3. The signal AUDIO TX is provided to VAD transmit channel 211 and to half-duplex transmit channel 201. Half-duplex channel 201 selectively passes on the signal AUDIO TX to compression unit 222 for transmission across the audio channel 95, depending upon an input TXO received from the VAD transmit channel 211 indicating whether or not speech is present in signal AUDIO TX. Referring now to FIG. 4B, if half-duplex transmit channel 201 receives an input TXO from VAD transmit channel 211 indicating that speech is present in signal AUDIO TX in step 404, then half-duplex transmit channel 201 communicates with half-duplex receive channel 200 to cause the half-duplex receive channel 200 to mute the speaker 52 in step 405. The speaker 52 remains muted until speech is no longer detected in the signal AUDIO TX.

Referring again to FIG. 2, autocalibrator 230 automatically calibrates headset 51 in response to a user input entered through a graphical user interface (GUI) 240 in a manner which is not dependent upon the particular make or model of headset 51. Autocalibrator 230 receives a user input UI from the GUI 240 and the signal TXO from the VAD transmit channel 211. Autocalibrator 230 outputs a first calibration signal CAL1 to the audio front-end input circuitry 253 and a second calibration signal CAL2 to the memory 40 and the disk storage device 20. The signal CAL1 is used to calibrate the audio front end input circuitry 253, and the signal CAL2 is used to store the appropriate hardware settings on the disk storage device 20 or in the memory 40.

Figure 4C:
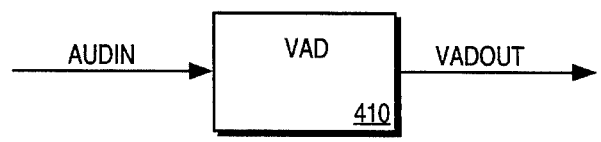
FIG. 4C is a block diagram of a voice activity detector.
Figure 5:
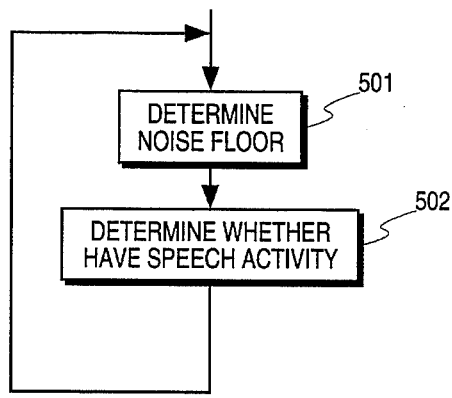
FIG. 5 is a flowchart illustrating the overall operation of a voice activity detector.

Although VAD receive channel 210 and VAD transmit channel 211 have thus far been illustrated and described separately, they perform essentially identical functions and are each hereinafter represented interchangeably by the VAD 410 illustrated in FIG. 4C. The VAD 410 receives an input audio signal AUDIN, which represents either signal AUDIO RX or signal AUDIO TX, and outputs a signal VADOUT, which represents either signal RXO or signal TXO and which indicates whether speech is present in the input signal AUDIN. Referring now to FIG. 5, a flow chart is shown illustrating the overall function of the VAD 410. The function of the VAD 410 consists generally of two steps. In step 501, a noise floor NF is established. Next, in step 502, the VAD 410 determines whether speech is present in the input signal AUDIN based upon the relationship of the input signal AUDIN to the noise floor NF. In the preferred embodiment, steps 501 and 502 are each repeated once every 20 milliseconds (msec).

Figure 6:
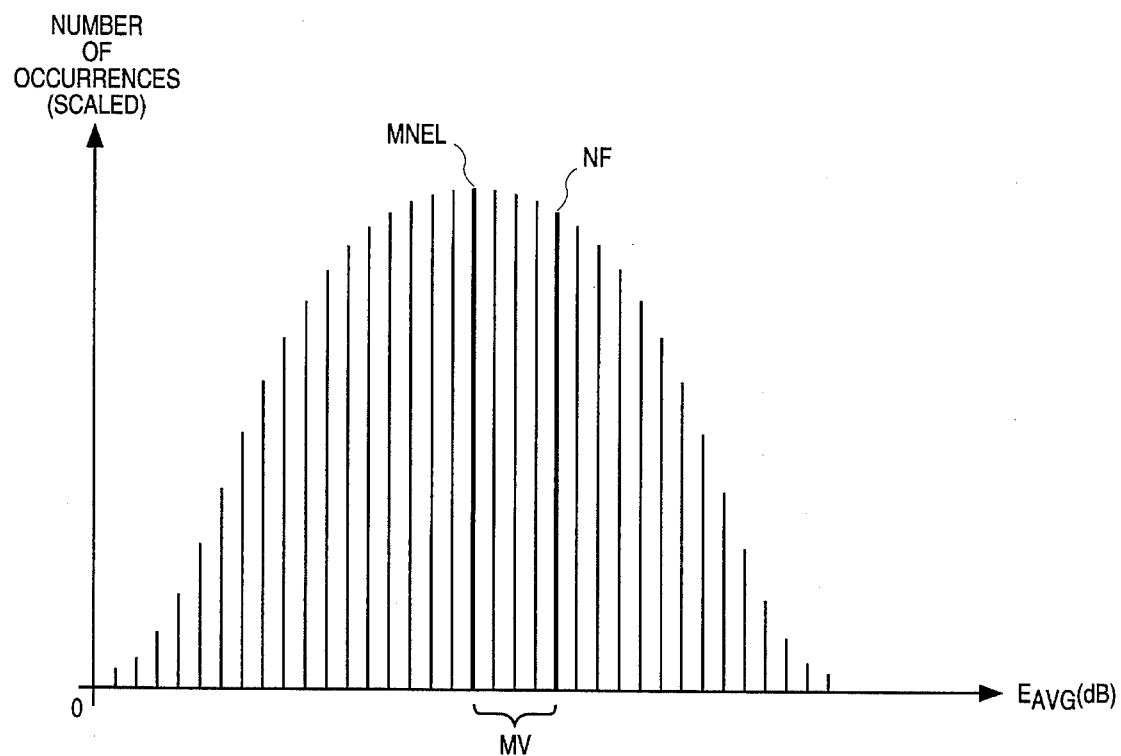
FIG. 6 illustrates a noise power density function.

The VAD 410 continuously recomputes the noise floor NF in determining whether speech is present in the input signal, as will be described in greater detail below. The noise floor is generated based on a noise power density function (NPDF) which is created and updated by the VAD 410. The energy level of the noise floor NF is based upon a current state of the NPDF at any given point and time. An example of an NPDF is illustrated in FIG. 6. The noise floor NF is taken to be the mean energy value of the NPDF, i.e., the mean noise energy level (MNEL), plus a margin value MV. In the preferred embodiment, the input signal AUDIN is sampled by the VAD 410 at a rate of 8 kHz and the NPDF is updated every 20 msec. Consequently, the input signal AUDIN is sampled 160 times for every 20 msec time interval.

Figure 9A:
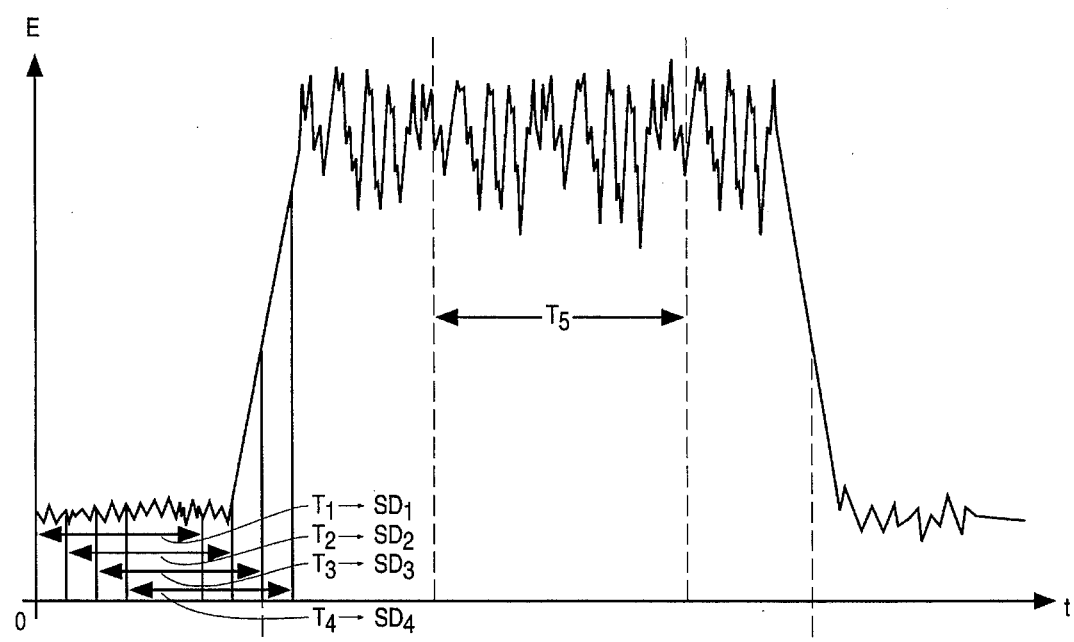
FIG. 9A illustrates an approach to calculating the standard deviation of an audio signal according to the present invention.

The VAD 410 uses both the standard deviation of the energy of the input signal over a period of time as well as the current energy level of the input signal at a particular point in time to update the NPDF. A "sliding window" of time is used in gathering samples of the input signal's energy to generate each new value of the standard deviation SD. That is, each calculated value of standard deviation SD is based upon a sample period which overlaps at least one previous sample period, as illustrated in FIG. 9A and as will be further discussed below. In the preferred embodiment, a sample period of 500 msec is used to generate each standard deviation value SD. This period of 500 msec is updated every 20 msec in order to achieve a fast response time of the VAD 410. Because such short time periods are used, the current energy level E is examined in comparison to an envelope of the input signal AUDIN as a means of increasing accuracy in updating the noise floor NF, i.e., to reduce the number of instances when low standard deviation speech is incorrectly interpreted as noise. In the preferred embodiment, the envelope of the input signal is an average peak AP of the input signal AUDIN over a two-second time window.

Figure 7:
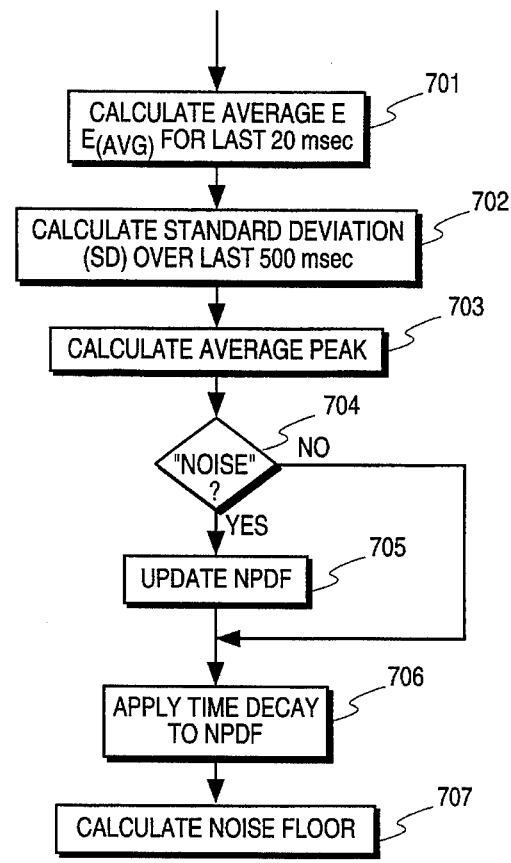
FIG. 7 is a flowchart illustrating a process of determining and updating a noise floor.

Referring now to FIG. 7, the process of determining and updating the noise floor NF (step 501) is illustrated in greater detail. The process consists of steps 701 through 707. As noted above, the overall function of the VAD 410 is a process which is repeated every 20 msec. Consequently, each of steps 701 through 705 is performed once every 20 msec. The VAD 410 samples the input signal AUDIN at a rate of 8 kHz, or 160 samples for each 20 msec iteration. For each sample, the energy level E of the input signal AUDIN is determined. In step 701, the average energy $E_{AVG}$ is calculated for all samples occurring during the last 20. In step 702, the standard deviation SD is calculated for all of the values of average energy $E_{AVG}$ computed during the last 500 msec. In step 703, the average peak AP of the input signal AUDIN is calculated. In step 704, the VAD makes a preliminary decision as to whether the input signal contains noise only or speech. This preliminary decision, however, is made only for the purpose of updating the noise floor NF and not for the purpose of making a final determination of whether speech is present in the input signal AUDIN. In step 705, the NPDF is updated if the outcome of the preliminary determination was that only noise is present in the input signal (step 704). If it is determined that not only noise is present, the NPDF is not updated. In step 706, a time decay function is applied to the NPDF to eliminate insignificant data points. This step consists of multiplying the entire NPDF curve by a value of 0.99990 resulting in approximately a one-half percent per second decay in each bin (energy value) of the NPDF. The effect of this time decay is that energy values which occur infrequently will eventually disappear from the NPDF or impact the NPDF less heavily than those that occur more frequently. In step 707, the noise floor NF is calculated as the mean energy level of the NPDF plus a margin value MV; that is, the noise floor NF equals the mean noise energy level (MNEL) plus the margin value MV (see FIG. 6). In the preferred embodiment, the margin value MV is 6 dB, however, this value may be tailored to meet desired performance characteristics.

Figure 8:
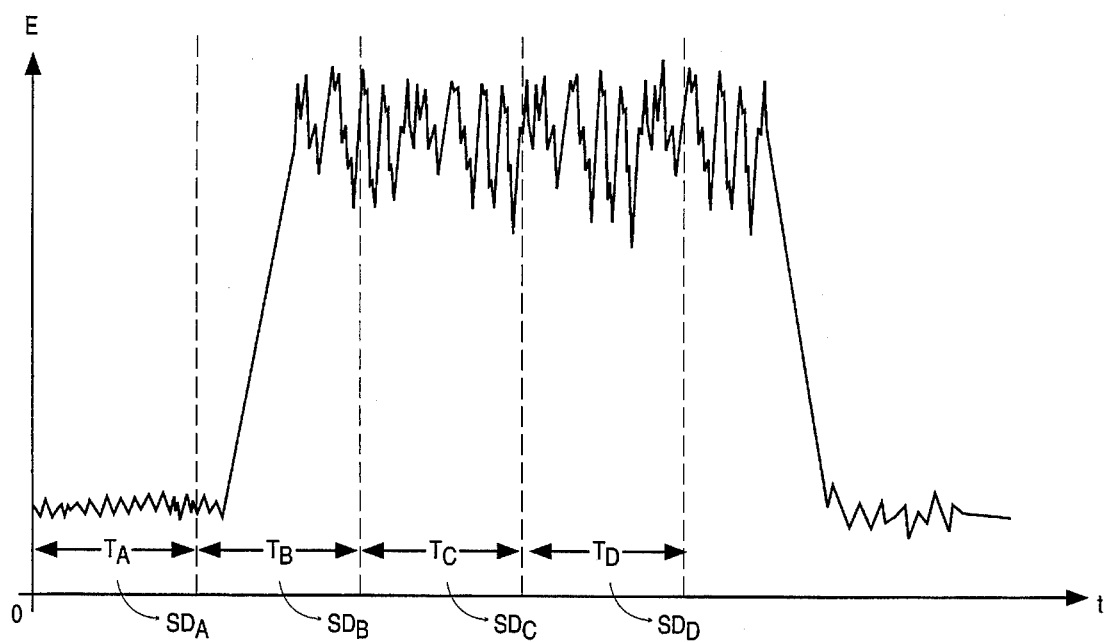
FIG. 8 illustrates a prior art approach to calculating the standard deviation of the energy of an input audio signal.

As mentioned above, the noise floor NF is updated based, in part, on the standard deviation SD of samples of the average energy $E_{AVG}$ of the input signal AUDIN. In particular, during a given time interval, a low standard deviation SD usually indicates a lack of speech activity (i.e., noise only) in the input signal AUDIN, assuming the duration of the sample window is long enough. By contrast, a high standard deviation in signal energy usually indicates that speech activity is present in the input signal. The standard deviation SD is computed according to the following formula:

$$SD = \sqrt{\frac{\sum_{i=1}^{n}(E_i - \overline{E}_i)^2}{n-1}}$$

where $\overline{E}_i$ represents values of average energy $E_{AVG}$. A new standard deviation value SD is calculated every 20 msec for the purpose of updating the NPDF. The standard deviation SD is calculated for all values of average energy $E_{AVG}$ occurring within the last 0.5 seconds. Referring to FIG. 9A, overlapping time intervals $T_1$ through $T_4$ are examples of four sample windows that are used to generate four consecutive standard deviation values, $SD_1$ through $SD_4$, respectively. Because a new value of standard deviation SD is calculated every 20 msec to update the noise floor NF, time intervals $T_1$ through $T_4$ are offset by increments of 20 msec. This method of calculating standard deviation SD differs from a prior art method, illustrated in FIG. 8, in which non-overlapping time intervals $T_A$ through $T_D$ are used to generate standard deviation values $SD_A$ through $SD_D$.

Figure 9B:
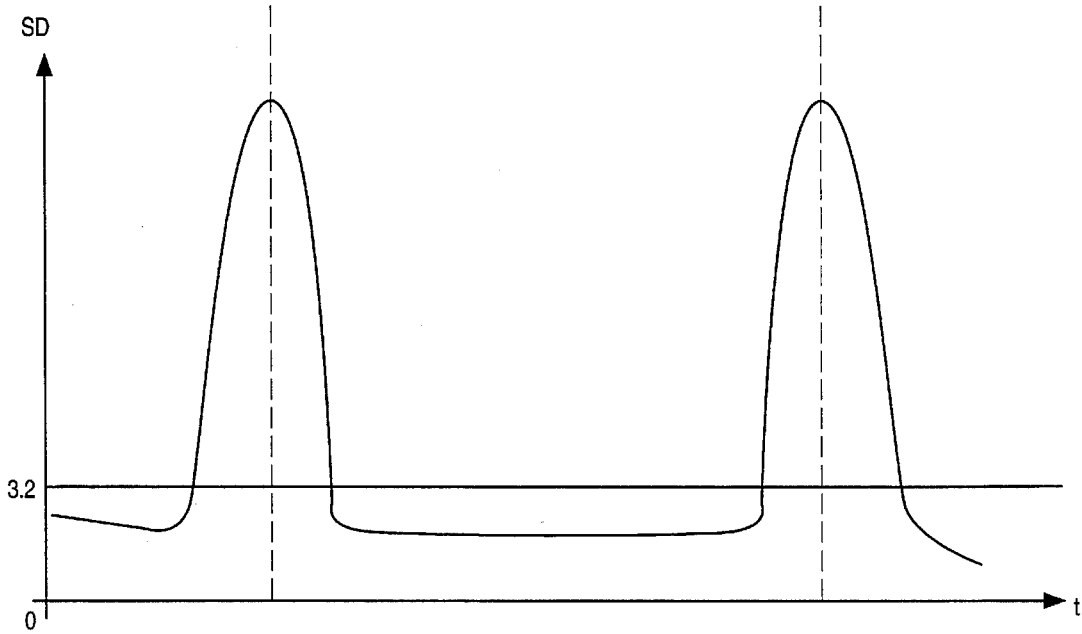
FIG. 9B illustrates a plot of the standard deviation of an input audio signal over time.
Figure 10:
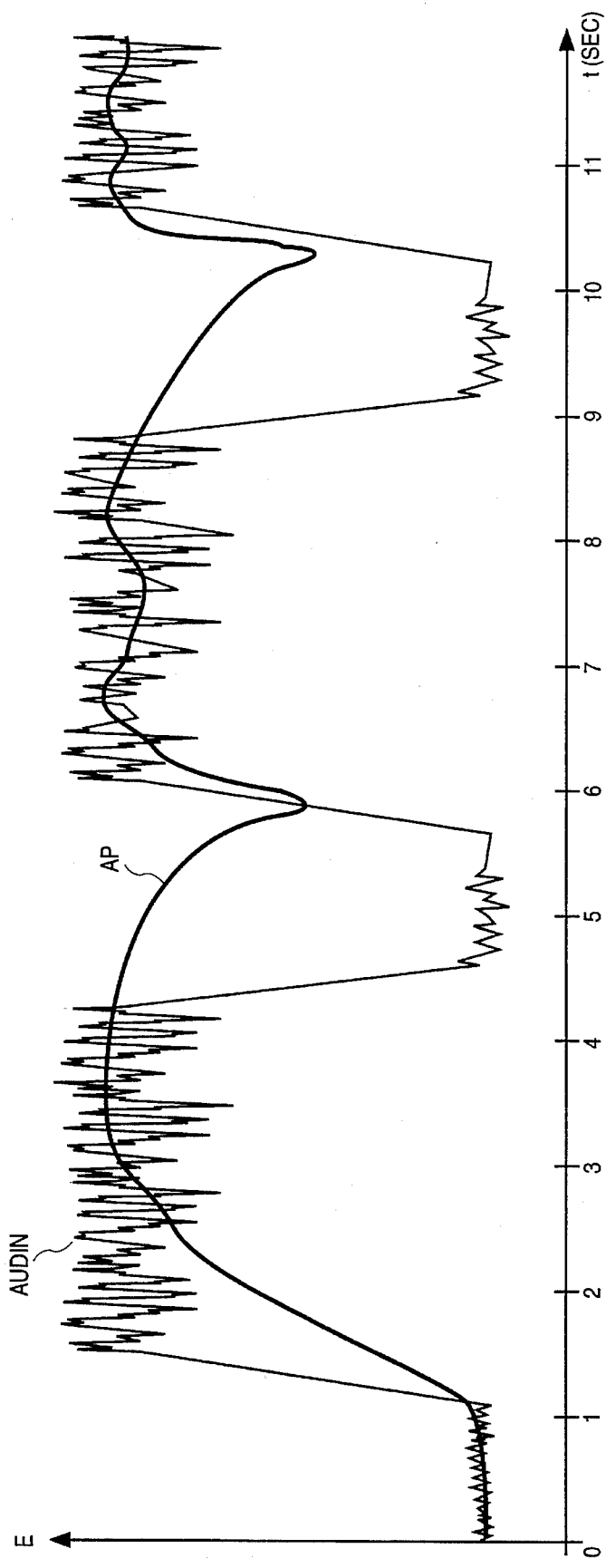
FIG. 10 illustrates a waveform of an input audio signal and a plot of the average peak of the input audio signal.

As noted above, the time interval of 500 msec used in the present invention for calculating the standard deviation SD is relatively short in view of the dynamic characteristics of typical human speech. That is, during a given 500 msec time period of continuous human speech, the standard deviation SD of the signal energy may be quite low, perhaps below whatever threshold value is being used. As the duration of the sample window for calculating standard deviation SD is reduced, the likelihood of misclassifying speech as noise tends to increase. This principle is illustrated in FIG. 9B, which shows a plot of standard deviation SD over time for the waveform shown in FIG. 9A. In the preferred embodiment, a standard deviation SD value of 3.2 is used as a threshold value in distinguishing speech from noise for the purpose of updating the NPDF. In FIGS. 9A and 9B, it can be seen that speech occurring during the time interval $T_5$ might be misclassified as noise if one relied only upon the standard deviation SD, since that value falls below 3.2 during the time interval $T_5$. Consequently, the present invention does not rely only upon the standard deviation SD of the input signal in classifying the input audio signal; instead, the present invention also computes an envelope of the input signal AUDIN during every 20 msec iteration as an additional factor in updating the NPDF. This envelope is represented by the average peak AP of the energy of the input signal AUDIN, as illustrated in FIG. 10.

Figure 11:
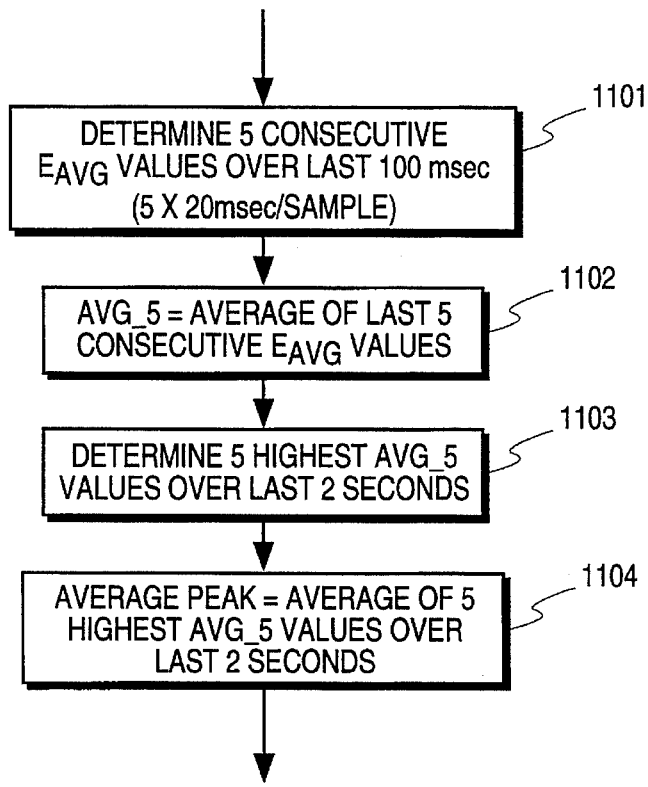
FIG. 11 is a flowchart illustrating a process of calculating an average peak of an input audio signal.

FIG. 11 illustrates a flow chart showing how the average peak AP is calculated. In step 1101, the last five consecutive average energy values $E_{AVG}$ (corresponding to the last 100 msec) are saved. These five $E_{AVG}$ values are then averaged in step 1102 to produce a value $AVG_5$. In step 1103, the highest five values of $AVG_5$ calculated during the last two seconds are identified. In step 1104, the average peak AP is calculated to be the average of these five highest $AVG_5$ values.

Referring once again to FIG. 7, a preliminary determination of whether or not the input signal includes speech is made in step 704 for the limited purpose of updating the NPDF (step 705) to update the noise floor NF (step 707). As already mentioned, the average peak AP is used, in part, to increase accuracy during time periods in which the standard deviation value falls below 3.2 even though speech is occurring. Specifically, the input signal AUDIN will not be determined to contain only noise unless the current value of average energy $E_{AVG}$ falls below the level of the current average peak AP minus 9 dB. Hence, an input signal AUDIN which has a low standard deviation SD but a high current average energy $E_{AVG}$ is unlikely to be misclassified as noise for the purpose of updating the NPDF. In addition, the present invention also employs a "zero-crossing" algorithm to further increase the accuracy of the noise floor, as is discussed below.

Figure 12:
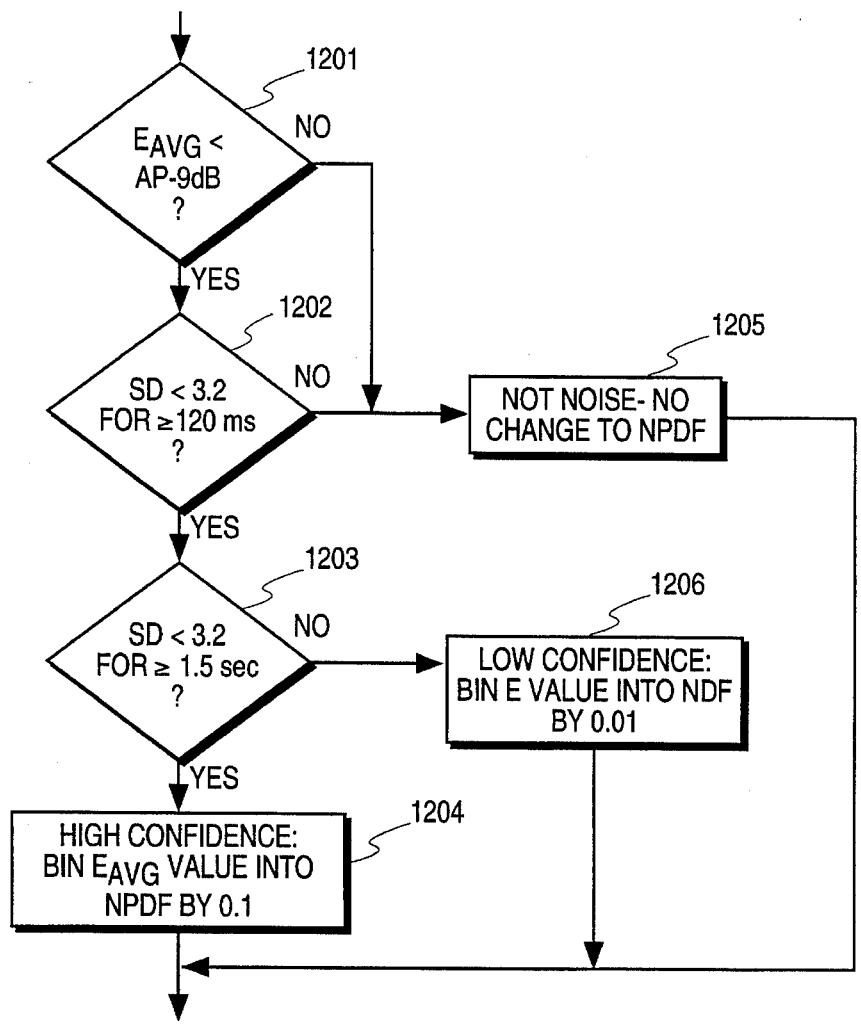
FIG. 12 is a flowchart illustrating a process of determining whether an input signal contains only noise and updating a noise power density function.

FIG. 12 is a flowchart showing in detail the steps of determining whether the input signal contains only noise (step 704) and updating the NPDF (step 705). In step 1201, if the current average energy $E_{AVG}$ does not fall below the level (AP- 9 dB), then it is determined in step 1205 that the input signal AUDIN is not noise for the purpose of updating the NPDF; in that case, no bin of the NPDF is increased. If, however, it is determined in step 1201 that the current average energy $E_{AVG}$ does fall below (AP- 9 dB), then a determination is made in step 1202 of whether all of the standard deviation values SD calculated during the last 120 msec have fallen below 3.2. If the outcome of step 1202 is "NO", then it is determined in step 1205 that the input signal AUDIN is not noise for the purpose of updating the NPDF, and no bin of the NPDF is increased. If all of the standard deviation values SD have fallen below 3.2 for at least the last 120 msec, then a determination is made in step 1203 of whether all of the standard deviation values SD have fallen below 3.2 for at least the last 1.5 seconds. If the outcome of step 1203 is "NO", then there is "low confidence" that the input signal AUDIN contains only noise. Consequently, in step 1206 the appropriate bin of the NPDF is updated by increasing that bin by a low confidence value of 0.01. If, however, in step 1203 the standard deviation SD has fallen below 3.2 for at least 1.5 seconds (and the outcomes of steps 1201 and 1202 was "YES"), then there is "high confidence" that the input signal AUDIN is noise only. In that case, the appropriate bin of the NPDF is increased by a high confidence value of 0.1 in step 1204. Note that it is not necessary to use the exact values of 0.01 as the low confidence value and 0.1 as the high confidence value in order to practice the present invention. The important aspect of these numbers is that the ratio of the high confidence value to the low confidence value is substantially greater than one. Hence, the NPDF is updated based upon both the relationship between the current average energy value $E_{AVG}$ of the input signal to the current average peak AP as well as the standard deviation SD of the input signal energy over a given time period. Each time a particular bin of the NPDF is increased, it is increased by either a high confidence value or a low confidence value to reflect the degree of confidence that the input signal AUDIN currently contains only noise.

Figure 13:
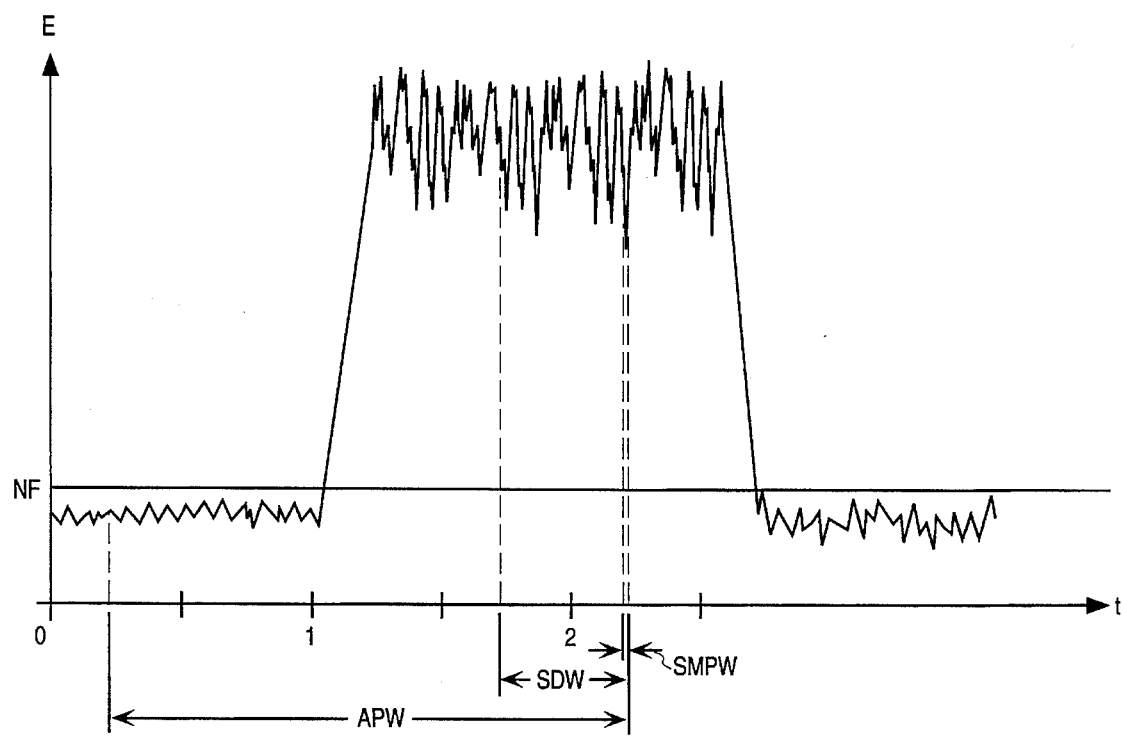
FIG. 13 illustrates a waveform of an input audio signal showing a comparison of the sample windows used in calculating average energy, standard deviation, and average peak of the input audio signal.

FIG. 13 shows an example of a waveform of the audio input signal AUDIN and the relationships between the sample windows used in calculating the average energy $E_{AVG}$, the standard deviation SD, and the average peak AP. In FIG. 13, an average energy value $E_{AVG}$ is calculated for samples of instantaneous energy E occurring within a 20 msec sample window SMPW. A standard deviation SD value is also calculated based upon values of $E_{AVG}$ calculated during the 0.5 second standard deviation window SDW. In addition, a new value of average peak AP is calculated based upon values of $E_{AVG}$ occurring during the two-second sample window APW. This process is repeated every 20 msec, with the sample windows SMPW, SDW, and APW being advanced by 20 msec for each repetition.

Figure 14:
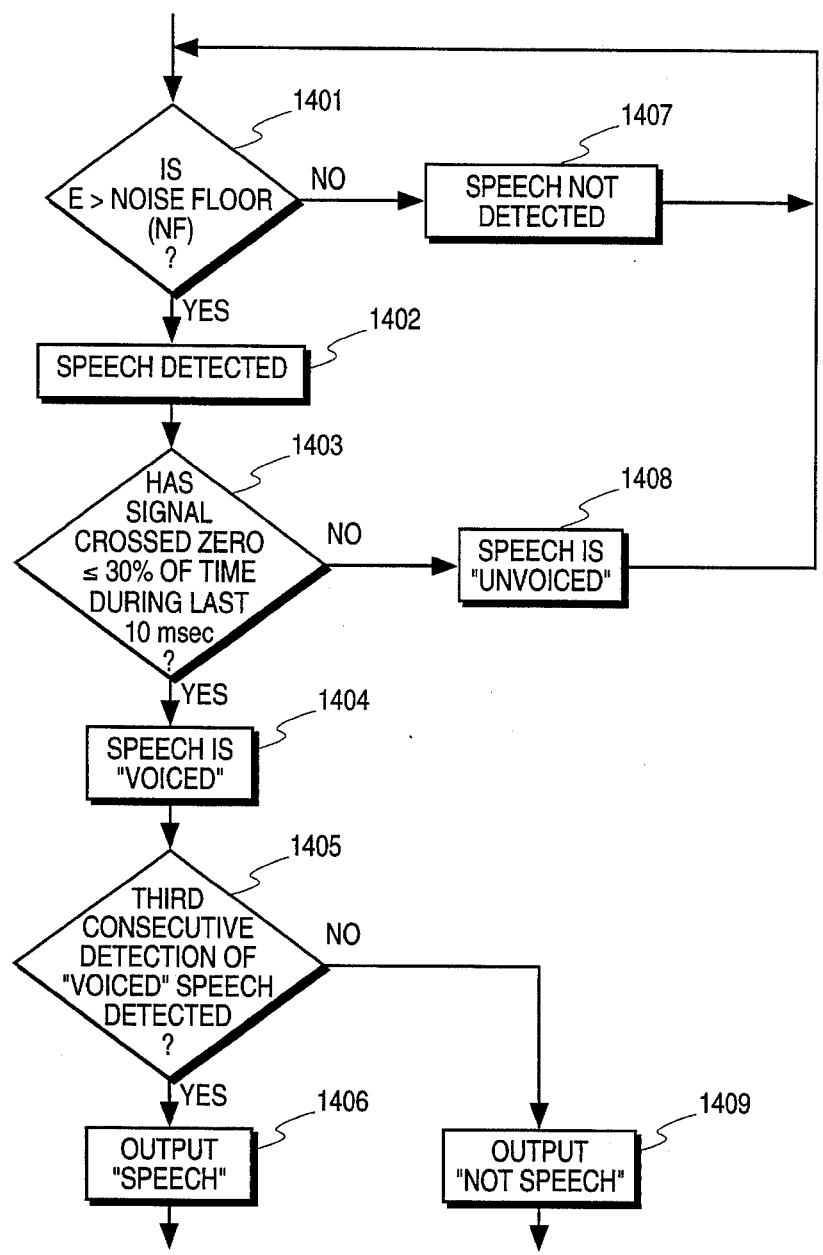
FIG. 14 is a flowchart illustrating a process for determining whether speech is present in an input audio signal.

The ultimate decision made by the VAD 410 as to whether or not the input signal AUDIN contains speech is indicated in the output signal VADOUT, which can be used to selectively mute the speaker 52 or the microphone 53 during open audio communication, based upon the current instantaneous energy E of the input signal relative to the noise floor NF. This decision-making process is illustrated in FIG. 14. In step 1401, a determination is made of whether the instantaneous energy E of the input signal AUDIN exceeds the noise floor NF. If not, then in step 1407 the VAD 410 makes the preliminary decision that speech is not detected in the input signal. If the instantaneous energy E exceeds the noise floor NF, then the VAD 410 makes the preliminary decision in step 1402 that speech is detected in the input signal AUDIN. If speech is detected in step 1402, a "zero-crossing" test is applied in step 1403 to determine whether the speech is "voiced" or "unvoiced" speech. "Voiced" speech is speech produced by vocal chord movement (e.g., the sound "Aaaah"), whereas "unvoiced" speech is speech produced without vocal chord movement (e.g., the sound "Shhhh"). The outcome of the zero-crossing test (step 1403) is used by the autocalibrator 230, as will be discussed further below. The final decision made by the VAD is "smoothed" by 60 msec. That is, in order for the VAD 410 to generate an output VADOUT indicating that speech is present in the input signal AUDIN (steps 1405, and 1406), three consecutive detections of speech corresponding to three consecutive 20 msec time intervals must occur in steps 1402 through 1404.

A zero-crossing test is well-known in the art of audio system design. The zero-crossing test of step 1403 is a determination of whether the raw signal value of the signal AUDIN has changed sign more than 30 percent of the time for the last 10 msec. In other words, between two consecutive samples of the input signal AUDIN, there may or may not be a change in sign; the test of step 1403 determines whether more than 30 percent of all of the pairs of consecutive samples of signal AUDIN occurring within the last 10 msec involved a sign change. If the signal AUDIN has changed sign more than 30 percent of the time during the last 10 msec, then it is determined in step 1408 that the detected speech is "unvoiced" speech. Otherwise, it is determined in step 1404 that the detected speech is "voiced" speech.

In addition to controlling muting of the speaker 52 and the microphone 53, the output of the VAD 410 may also be used in a feature which automatically establishes and implements the correct hardware settings for any headset which a user may wish to use. Referring once again to FIG. 2, the autocalibrator 230 receives the output TXO of the VAD transmit channel 211 as well as an input UI from the GUI 240. The user of the headset 51 clicks on an icon presented by the GUI 240 using the cursor control device 60 causing the GUI 240 to prompt the user to speak into the microphone of the headset 51 for a predetermined period of time. The autocalibrator 230 then adjusts the appropriate hardware settings, including the microphone input gain, and stores the settings in the memory 40, the disk storage device 20, or both.

Figure 15:
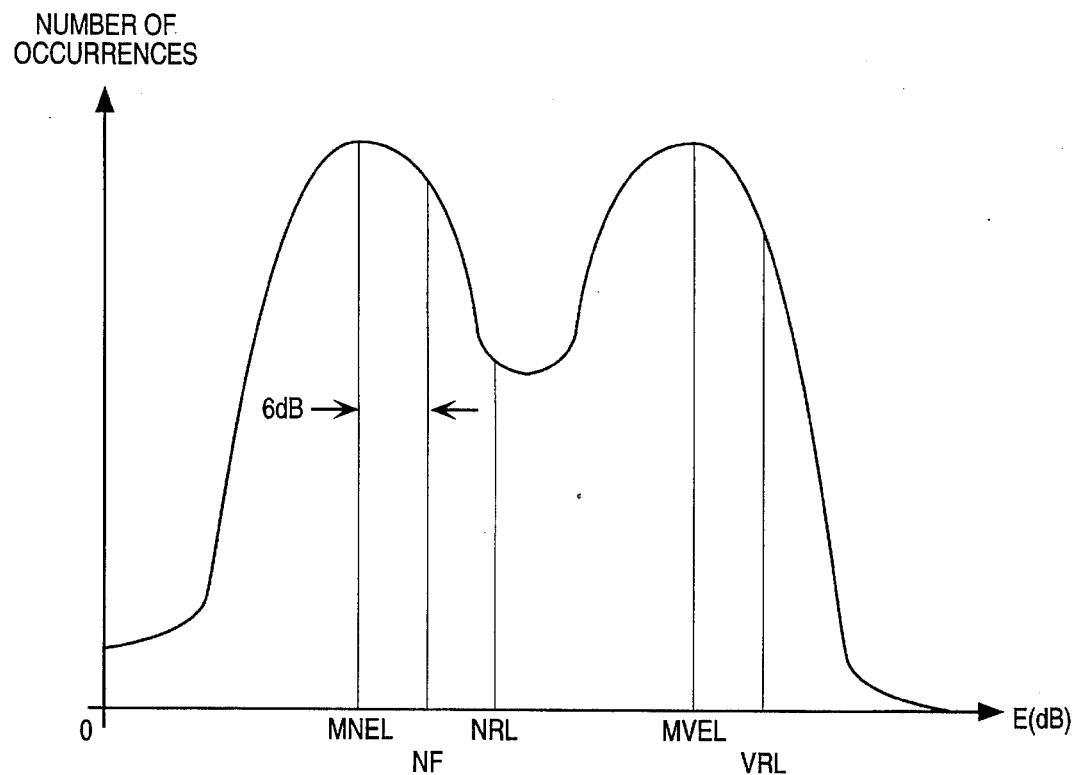
FIG. 15 illustrates a power density function of an input audio signal containing noise energy and speech energy.

As shown in FIG. 15, the input signal AUDIN to the VAD 410 can be represented as a double-humped power density curve of energy representing both noise and speech. Noise energy is concentrated around a MNEL and voice energy is concentrated around a mean voice energy level (MVEL). For a given headset, the microphone input gain may need to be increased so that a user on the receiving end can comfortably hear the voice of the user on the transmitting end. Hence, in the preferred embodiment, the microphone input gain is increased by autocalibrator 230 in response to the user's voice so that, in general, the MVEL of the input signal is raised to a predetermined voice reference level VRL. Increasing the microphone input gain, however, results in amplification of both noise energy and voice energy. Such amplification may have the undesirable effect of amplifying the noise energy level to an uncomfortable level. Consequently, a noise reference level NRL is established, and the microphone input gain is actually limited so that the noise floor NF does not exceed the noise reference level NRL. In the preferred embodiment, which has a total dynamic range of 95 dB, the voice reference level VRL is chosen to be 47 dB, while the noise reference level is chosen to be 32 dB.

Figure 16:
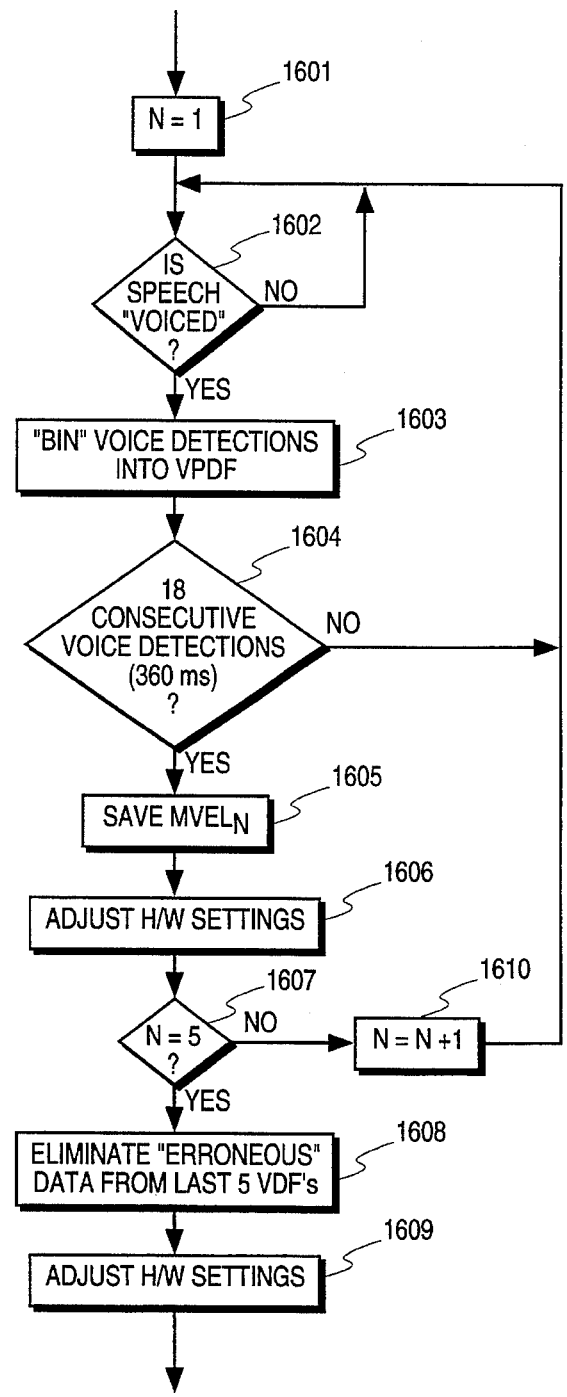
FIG. 16 is a flowchart illustrating a process for automatically calibrating a microphone of a headset.

FIG. 16 is a flowchart of the process used by autocalibrator 230 to calibrate the microphone of headset 51. Autocalibrator 230 uses the TXO output of the VAD transmit channel 211 to create and maintain several voice power density functions (VPDFs). In step 1602, the autocalibrator 230 determines whether the input signal AUDIN currently contains either voiced or unvoiced speech based on the outcome of the zero-crossing test (see FIG. 14). In step 1603, instances of voiced speech are binned into a VPDF based on the output of the VAD transmit channel 211. The autocalibrator 230 continues binning instances of voiced speech into the VPDF until a well-distributed (useful) VPDF is generated. The well-distributed VPDF consists of 18 instances of voiced speech detected at 20 msec intervals, i.e., 360 msec of detected voiced speech (step 1604). Once the VPDF is generated, the mean voice energy level MVEL of that VPDF is saved in step 1605. In step 1606, the hardware settings are adjusted based on the MVEL of the VPDF, in the manner described above. This process is repeated until five separate VPDFs have been created to generate five separate MVELs (MVEL$_1$, MVEL$_2$, ..., MVEL$_5$), each consisting of 18 consecutive voice detections. After generating five separate VPDFs and adjusting the hardware settings each time, a correction is made in step 1608 to eliminate certain data points from the VPDFs which are likely to be erroneous. After erroneous data is eliminated, the hardware settings are adjusted one final time in step 1609 to complete the automatic calibration process.

Figure 17:
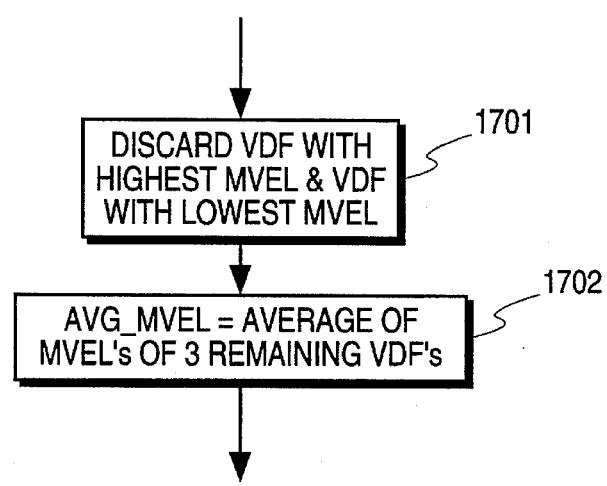
FIG. 17 is a flowchart illustrating a process for eliminating erroneous data during automatic calibration of a microphone.

FIG. 17 shows in greater detail the step (1608) of eliminating erroneous data. In step 1701, of the five VPDFs which have been saved, the VPDF having the highest MVEL and the VPDF having the lowest MVEL are discarded. The MVELs of the three remaining VPDFs are then averaged in step 1702 to generate a value AVG_MVEL. The value AVG_MVEL is used to make the final adjustment of the hardware settings.

Figure 18A:
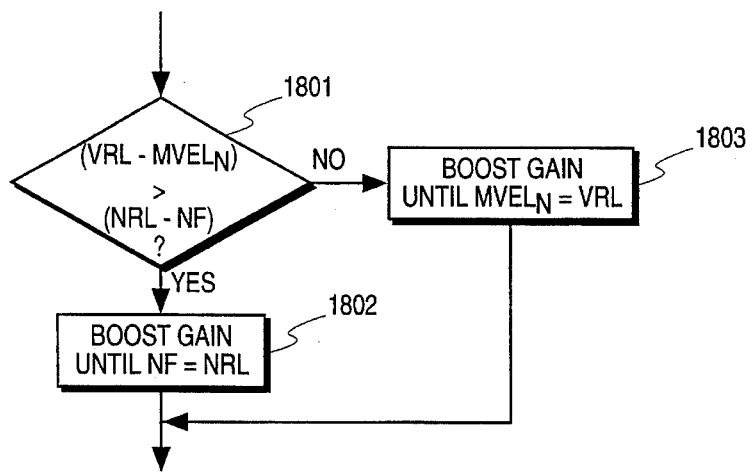
FIGS. 18A and 18B illustrate processes for adjusting hardware settings during automatic calibration of a microphone.
Figure 18B:
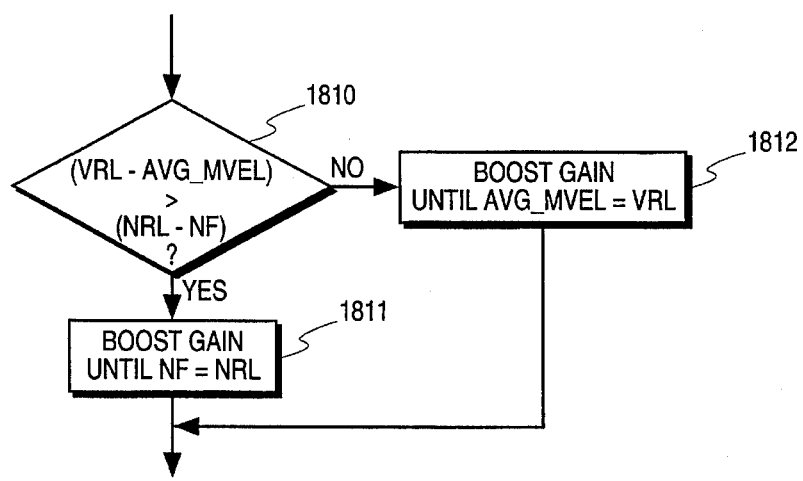

FIGS. 18A and 18B illustrate in greater detail steps 1606 and 1609 of adjusting the hardware settings, respectively. Referring to FIG. 18A, a determination is made in step 1801 as to whether the difference between the voice reference level VRL and the MVEL of the most recently-generated VPDF exceeds the difference between the noise reference level NRL and the noise floor NF, i.e., whether (VRL–MVEL$_N$)>(NRL–NF). If this condition is true, then in step 1802 the gain increased until the noise floor NF equals the noise reference level NRL. If the condition is not true, then the gain is increased until the MVEL of the most recently-generated VPDF equals the voice reference level VRL (i.e., until MVEL$_N$=VRL).

The adjustment of hardware settings performed in step 1609 differs somewhat from that performed in step 1606. Referring to FIG. 18B, a determination is made in step 1810 as to whether the difference between the voice reference level VRL and the value AVG_MVEL exceeds the difference between the noise reference level NRL and the noise floor NF, i.e., whether (VRL–AVG_MVEL)>(NRL–NF). If this condition is true, then the gain is increased in step 1811 until the noise floor NF equals the noise reference level NRL. If not, then the gain is increased in step 1812 until the value AVG_MVEL equals the voice reference level VRL. Hence, the autocalibrator 230 automatically adjusts the hardware settings as appropriate for the particular headset 51 being used.

Hence, what has been described is a VAD which operates independently of a remote site. The VAD provides high accuracy, fast response time, capability to adapt to the remote site's signal-to-noise ratio, as well as consistent half-duplex performance when the remote user transitions between opened and closed audio modes. Also, a hardware calibration solution has been described which automatically adjusts the hardware settings to be appropriate for any headset.

Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of locating a noise floor for qualifying a signal, comprising the steps of:

establishing a noise power density function (NPDF), based on:

a relationship between an approximate peak level of the signal and a current level of the signal, and a plurality of standard deviation values of the signal, each of the standard deviation values corresponding to one of a plurality of time intervals;

repeatedly updating the NPDF to produce a current state of the NPDF; and using the current state of the NPDF to locate the noise floor.

2. The method according to claim 1, wherein each of the time intervals overlaps at least one other time interval.

3. The method according to claim 1, wherein the step of repeatedly updating comprises the steps of:

determining whether the approximate peak level of the signal exceeds the current level of the signal by a predetermined amount;

determining whether all of the standard deviation values calculated during a first time period are below a threshold value; and identifying a noise instance if:

the approximate peak level of the signal exceeds the current level of the signal by a predetermined amount, and all of the standard deviation values calculated during the first time period are below the threshold value.

4. The method according to claim 1, wherein the approximate peak level corresponds to an envelope of the signal.

5. A method of detecting speech in an audio signal, comprising the steps of:

determining an average peak of the audio signal; determining a plurality of standard deviation values of the audio signal, each of the standard deviation values corresponding to one of a plurality of time intervals;

updating a power density function (PDF) to establish a current state of the PDF according to a relationship between the average peak and a current level of the audio signal and based on the standard deviation values;

locating a noise floor based on the current state of the PDF; and if a predetermined relationship exists between the current level of the audio signal and the noise floor, determining that speech is represented in the audio signal.

6. The method according to claim 5, wherein each of the time intervals overlaps at least one other time interval.

7. The method according to claim 5, wherein the PDF represents a plurality of noise instances.

8. The method according to claim 7, wherein the updating step comprises the steps of:

determining whether the average peak of the audio signal exceeds the current level of the audio signal by a predetermined amount;

determining whether all of the standard deviation values calculated during a first time period are below a threshold value; and identifying a noise instance if:

the average peak of the audio signal exceeds the current level of the audio signal by a predetermined amount, and all of the standard deviation values calculated during the first time period are below the threshold value.

9. The method according to claim 8, wherein the updating step further comprises the step of modifying the PDF to reflect an additional noise instance if a noise instance was identified.

10. The method according to claim 9, wherein the modifying step comprises the steps of:

modifying the PDF according to a low confidence factor if all of the standard deviation values calculated during the first time period are below the threshold value; and modifying the PDF according to a high confidence factor if all of the standard deviation values calculated during a second time period are below the threshold value, wherein the second time period is greater than the first time period.

11. The method according to claim 5, wherein the average peak corresponds to an envelope of the audio signal.

12. The method according to claim 5, wherein the predetermined relationship is a relationship in which the current level exceeds the noise floor by a predetermined amount.

13. An apparatus for determining whether voice is present in an audio signal, comprising:

a peak calculator determining a peak of the audio signal;

a standard deviation generator determining a plurality of standard deviation values of the audio signal, each of the standard deviation values corresponding to one of a plurality of time intervals;

updating logic coupled to receive the peak and the standard deviation values, the updating logic updating a power density function (PDF) to establish a current state of the PDF according to a relationship between the peak and a current level of the audio signal and based on the standard deviation values;

a noise floor locator coupled to receive the current state of the PDF, the noise floor locator locating a noise floor based on the current state of the PDF; and decision logic coupled to receive the noise floor and the audio signal, the decision logic determining that voice is represented in the audio signal when a predetermined relationship exists between the current level of the audio signal and the noise floor.

14. The apparatus according to claim 13, wherein each of the time intervals overlaps at least one other time interval.

15. The apparatus according to claim 14, wherein the PDF represents a plurality of noise instances.

16. The apparatus according to claim 15, wherein the updating logic comprises:

first comparator logic determining whether the peak of the audio signal exceeds the current level of the audio signal by a predetermined amount;

second comparator logic determining whether all of the standard deviation values calculated during a first time period are below a threshold value; and noise logic coupled to the first comparator logic and the second comparator logic, the noise logic identifying a noise instance if:

the peak of the audio signal exceeds the current level of the audio signal by a predetermined amount, and all of the standard deviation values calculated during the first time period are below the threshold value.

17. The apparatus according to claim 15, wherein the peak corresponds to an envelope of the audio signal.

18. An apparatus for detecting voice in an audio signal, comprising:

means for determining an average peak of the audio signal;

means for determining a plurality of standard deviation values of the audio signal, each of the standard deviation values corresponding to one of a plurality of time intervals;

means for updating a power density function (PDF) to establish a current state of the PDF according to a relationship between the average peak and a current level of the audio signal and based on the standard deviation values;

means for locating a noise floor based on the current state of the PDF; and means for determining that voice is represented in the audio signal if a predetermined relationship exists between the current level of the audio signal and the noise floor.

19. The apparatus according to claim 18, wherein each of the time intervals overlaps at least one other time interval.

20. The apparatus according to claim 18, wherein the PDF represents a plurality of noise instances.

21. The apparatus according to claim 20, wherein the means for updating comprises:

means for determining whether the average peak of the audio signal exceeds the current level of the audio signal by a predetermined amount;

means for determining whether all of the standard deviation values calculated during a first time period are below a threshold value; and means for identifying a noise instance if:

the average peak of the audio signal exceeds the current level of the audio signal by a predetermined amount, and all of the standard deviation values calculated during the first time period are below the threshold value.

22. The apparatus according to claim 21, wherein the means for updating further comprises means for modifying the PDF to reflect an additional noise instance if a noise instance was identified.

23. The apparatus according to claim 22, wherein the means for modifying comprises:

means for modifying the PDF according to a low confidence factor if all of the standard deviation values calculated during the first time period are below the threshold value; and means for modifying the PDF according to a high confidence factor if all of the standard deviation values calculated during a second time period are below the threshold value, wherein the second time period is greater than the first time period.

24. The apparatus according to claim 20, wherein the average peak corresponds to an envelope of the audio signal.

25. A computer system having capability for duplex audio communication with a remote site, the system comprising:

a processor controlling the computer system;

an input device coupled to the processor and coupled to input audio information to be transmitted to the remote site;

an output device coupled to the processor and coupled to output audio information received from the remote site; and a voice activity detector coupled to the input device and the output device, the voice activity detector detecting voice represented in an audio signal received by the computer system or to be transmitted by the computer system, the voice activity detector including:

peak logic determining an average peak of the audio signal;

a standard deviation generator determining a plurality of standard deviation values of the audio signal, each of the standard deviation values corresponding to one of a plurality of time intervals;

updating logic coupled to receive the standard deviation values and the average peak updating a power density function (PDF) to establish a current state of the PDF according to a relationship between the average peak and a current level of the audio signal and based on the standard deviation values;

noise logic locating a noise floor based on the current state of the PDF; and decision logic determining that voice is represented in the audio signal when a predetermined relationship exists between the current level of the audio signal and the noise floor.

26. The computer system according to claim 25, wherein each of the time intervals overlaps at least one other time interval.

27. A processing system having capability for duplex audio communication with a remote site, the system comprising:

processor means for controlling the processing system;

input means for inputting audio information to be transmitted to the remote site;

output means for outputting audio information received from the remote sight; and voice detection means for detecting voice in an audio signal received by the processing system or to be transmitted by the processing system, the voice detection means including:

means for determining an approximate peak of the audio signal;

means for determining a plurality of standard deviation values of the audio signal, each of the standard deviation values corresponding to one of a plurality of time intervals;

means for updating a power density function (PDF) to establish a current state of the PDF according to a relationship between the approximate peak and a current level of the audio signal and based on the standard deviation values;

means for locating a noise floor based on the current state of the PDF; and means for determining that voice is represented in the audio signal if a predetermined relationship exists between the current level of the audio signal and the noise floor.

28. The processing system according to claim 27, wherein each of the time intervals overlaps at least one other time interval.

29. The processing system according to claim 27, wherein the PDF represents a plurality of noise instances.

30. The processing system according to claim 27, wherein the means for updating comprises:

means for determining whether the approximate peak of the audio signal exceeds the current level of the audio signal by a predetermined amount;

means for determining whether all of the standard deviation values calculated during a first time period are below a threshold value; and means for identifying a noise instance if:

the approximate peak of the audio signal exceeds the current level of the audio signal by a predetermined amount, and all of the standard deviation values calculated during the first time period are below the threshold value.

31. The processing system according to claim 30, wherein the means for updating further comprises means for modifying the PDF to reflect an additional noise instance if a noise instance was identified.

* * * * *